(12) United States Patent
Lewis et al.

(10) Patent No.: US 10,156,307 B2
(45) Date of Patent: *Dec. 18, 2018

(54) BUTTON LATCH WITH INTEGRALLY MOLDED CANTILEVER SPRINGS

(71) Applicant: General Electric Company, Schenectady, NY (US)

(72) Inventors: Peter D. Lewis, Fort Collins, CO (US); Carl T. Whitaker, Berthoud, CO (US); Riley M. Phipps, Fort Collins, CO (US)

(73) Assignee: General Electric Company, Schenectady, NY (US)

( * ) Notice: Subject to any disclaimer, the term of this patent is extended or adjusted under 35 U.S.C. 154(b) by 117 days.

This patent is subject to a terminal disclaimer.

(21) Appl. No.: 15/272,336

(22) Filed: Sep. 21, 2016

(65) Prior Publication Data

US 2017/0009919 A1    Jan. 12, 2017

Related U.S. Application Data

(63) Continuation of application No. 12/976,943, filed on Dec. 22, 2010, now Pat. No. 9,464,741.

(60) Provisional application No. 61/361,228, filed on Jul. 2, 2010, provisional application No. 61/289,998, filed on Dec. 23, 2009.

(51) Int. Cl.
| F16L 37/56 | (2006.01) |
| F16L 37/084 | (2006.01) |
| A61M 39/10 | (2006.01) |
| A61B 5/022 | (2006.01) |

(52) U.S. Cl.
CPC ......... *F16L 37/0841* (2013.01); *A61B 5/022* (2013.01); *A61M 39/105* (2013.01); *A61M 39/1011* (2013.01); *F16L 37/56* (2013.01); *A61M 2039/1027* (2013.01); *A61M 2039/1044* (2013.01); *A61M 2039/1083* (2013.01); *A61M 2039/1088* (2013.01)

(58) Field of Classification Search
CPC .... F16L 37/0871; F16L 37/56; A61M 39/105; A61M 39/1011; A61M 2039/1083; A61M 2039/1027; A61M 2039/1044
USPC ...................... 285/84, 85, 308, 319; 604/414
See application file for complete search history.

(56) References Cited

U.S. PATENT DOCUMENTS 7,802,822 B2 * 9/2010 Poder .................. F16L 37/0841
                                                    285/317
9,464,741 B2 * 10/2016 Lewis ................. F16L 37/0841

* cited by examiner

*Primary Examiner* — David Bochna
(74) *Attorney, Agent, or Firm* — Andrus Intellectual Property Law, LLP

(57) ABSTRACT

An integral button latch is formed for use in a female fluid connector housing. The button latch has a latch plate, a button actuator, and two or more cantilevered leg springs extending from beneath the actuation surface to interface with the connector housing. The latch plate, the button actuator, and the leg springs are all integrally formed. The leg springs bias the latch plate in a locked position and resist depression forces applied to either of the button actuator or the latch plate. By integrally forming the button latch structure, the cost associated with purchasing the springs, molding the lock latch, and the ensuing assembly of the three is significantly diminished.

26 Claims, 12 Drawing Sheets

BUTTON LATCH WITH INTEGRALLY MOLDED CANTILEVER SPRINGS

CROSS REFERENCE TO RELATED APPLICATIONS

This application is a continuation of U.S. patent application Ser. No. 12/976,943, filed Dec. 22, 2010, and published as U.S. Patent App. Pub. No. 2011/0210541 on Sep. 1, 2011, which claims the benefit of U.S. Provisional Patent App. No. 61/361,228, filed Jul. 2, 2010, and U.S. Provisional Patent App. No. 61/289,998, filed Dec. 23, 2009, which are hereby incorporated herein by reference in their entirety.

This application is also related to U.S. Provisional Patent App. No. 61/289,990, filed Dec. 23, 2009, U.S. Provisional Patent App. No. 61/289,545, filed Dec. 23, 2009, U.S. Design patent application Ser. No. 29/352,637, filed Dec. 23, 2009, and issued as U.S. Design Pat. No. D650,478 on Dec. 13, 2011, and U.S. Design patent application Ser. No. 29/351,665, filed Dec. 9, 2009, and issued as U.S. Design Pat. No. D649,240 on Nov. 22, 2011, which are hereby incorporated herein by reference in their entirety.

TECHNICAL FIELD

The technology described herein relates to latch mechanisms for fluid tube connection devices.

BACKGROUND

Tubing sections are often be joined together to provide for gas and/or liquid fluid flow from one component to another. Thus, it is often desirable to connect and disconnect tubing sections from one another. For example, when a patient's blood pressure is taken with an automatic blood pressure monitor, tubing from the blood pressure cuff (which is generally wrapped around the patient's arm) is connected to the tubing that is connected to the blood pressure monitor. To disconnect the cuff from the blood pressure monitor, it is desirable to merely detach the tubing section connected to the cuff from the tubing connected to the blood pressure monitor. Similarly, when providing intravenous fluids, it is often required to replace an empty fluid bag with a full fluid bag without removing the intravenous needle or stent from the patient. In order to switch between the first fluid bag and the second fluid bag, it is desirable to merely detach a tubing section connected with the fluid bag to the tubing section connected with the needle or stent placed intravenously in the patient, which can then be easily connected with a tubing section connected with the new fluid bag.

Single lumen blood pressure cuff connectors are commercially available from various manufacturers. Common connectors currently use two metal springs and a separate molded lock latch part in conjunction with the disconnect button to form a button-actuated latch mechanism. Generally, the greater number of parts forming a connector, the more expensive it will be to manufacturer due to the cost of multiple parts and the greater number of steps in the manufacturing and assembly process.

The information included in this Background section of the specification, including any references cited herein and any description or discussion thereof, is included for technical reference purposes only and is not to be regarded subject matter by which the scope of the invention is to be bound.

SUMMARY

An integral button latch is formed in a female fluid connector housing having a latch plate, an actuator portion, and two or more cantilevered springs extending from beneath the actuation surface. The latch plate is integral with and extends downwardly from the button actuator. The leg springs are integrally formed with either or both the button actuator and the latch plate and extend from either or both the button actuator or the latch plate. The plurality of cantilevered leg springs bias the latch plate in a locked position and resist depression forces applied to each of the button actuator and the latch plate.

By integrally forming the button latch structure, the separate costs associated with purchasing the springs, molding the lock latch and the ensuing assembly of the three is significantly diminished. In one implementation, the button latch is designed with three plastic springs and a dual latch, which are all molded as part of a single disconnect button. The four parts (button, 2 springs, and the lock latch) are thus consolidated into one button latch. As a further advantage, by designing a connector with no metal springs, the connector is compatible for use during a magnetic resonance imaging (MRI) procedure or in other environments in which metal parts or multiple parts might malfunction or become hazardous.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

Figure 1:
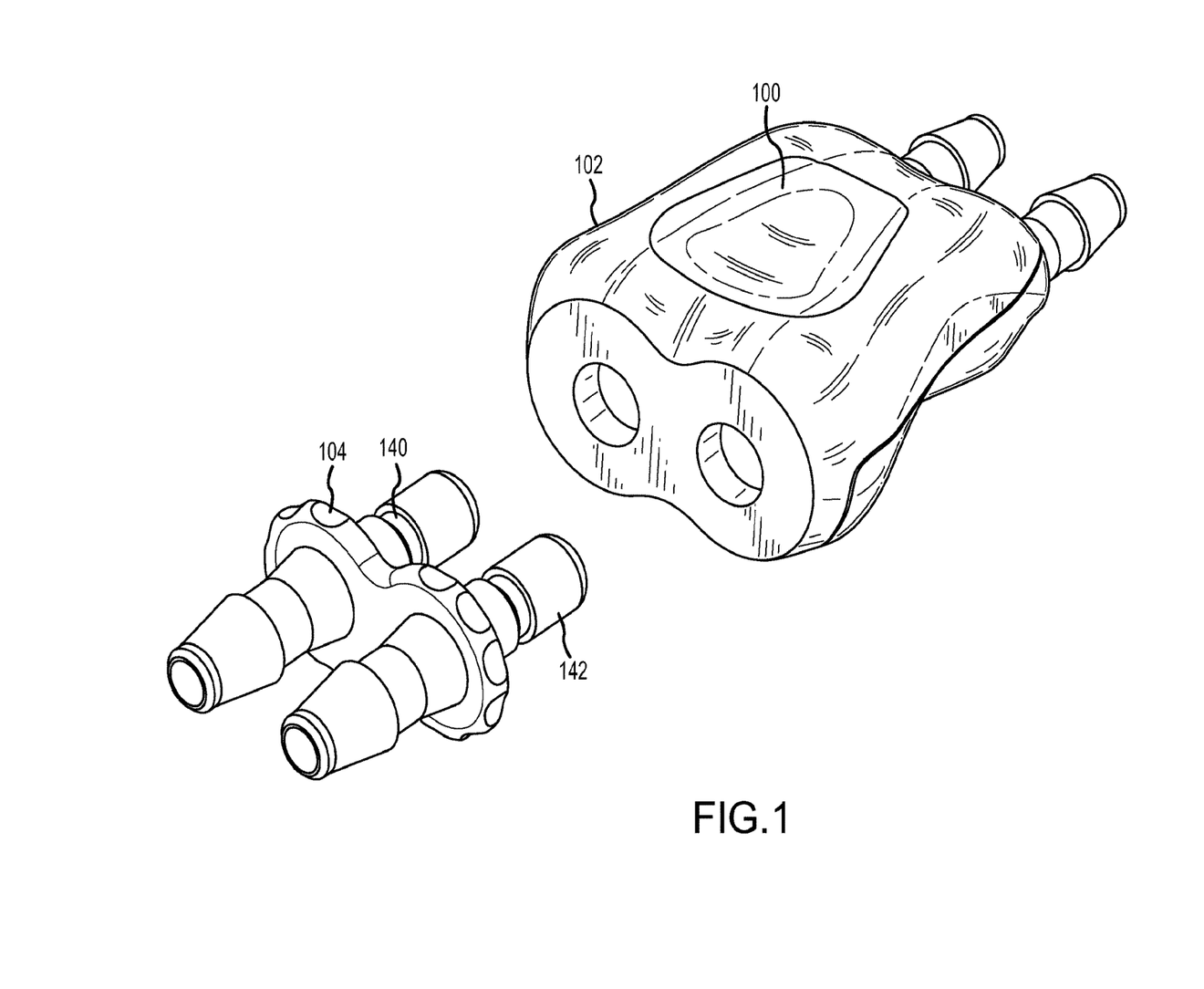
FIG. 1 is an isometric view of a female connector with a button latch and a corresponding male bayonet connector.
Figure 2A:
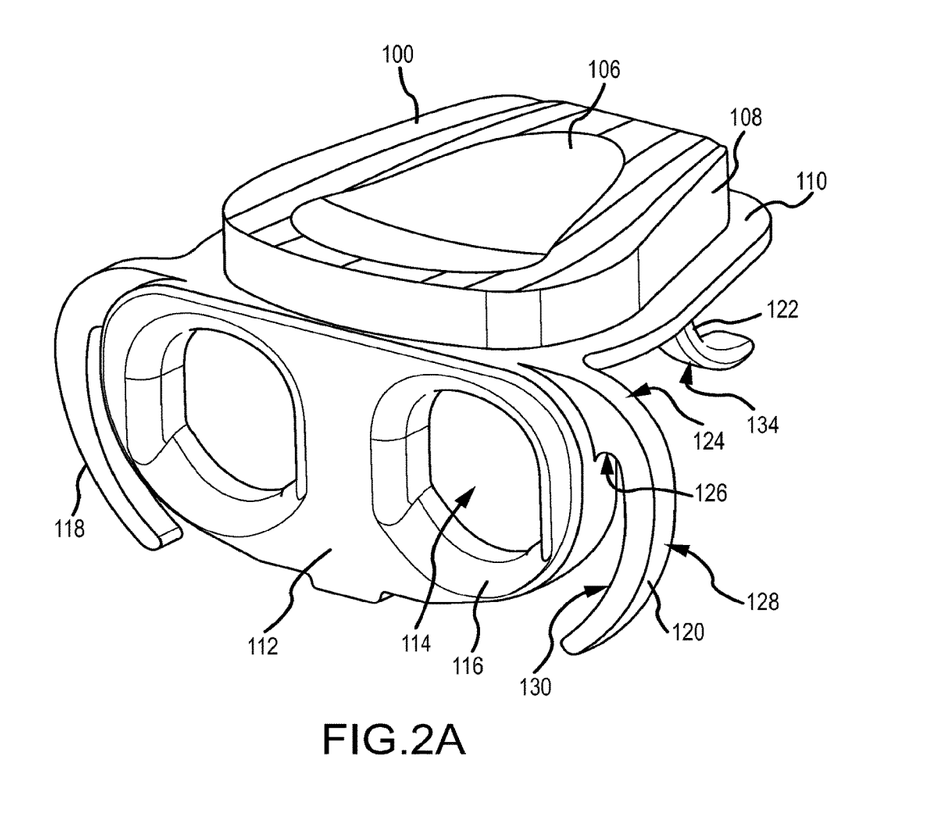
FIG. 2A is a top front isometric view of an embodiment of a button latch with integrally molded cantilevered springs.
Figure 2B:
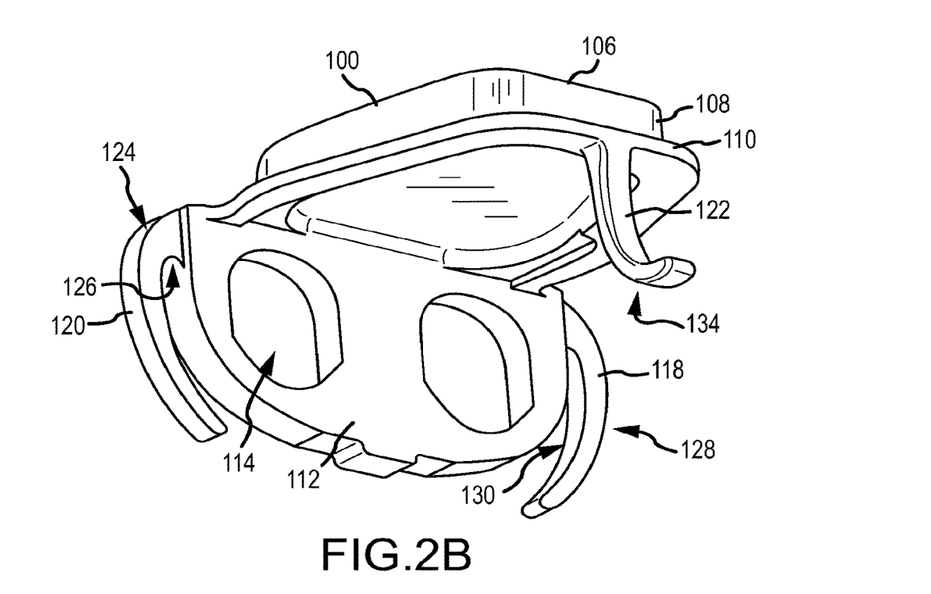
FIG. 2B is a bottom rear isometric view of the button latch of FIG. 2A with integrally molded cantilevered springs.
Figure 2C:
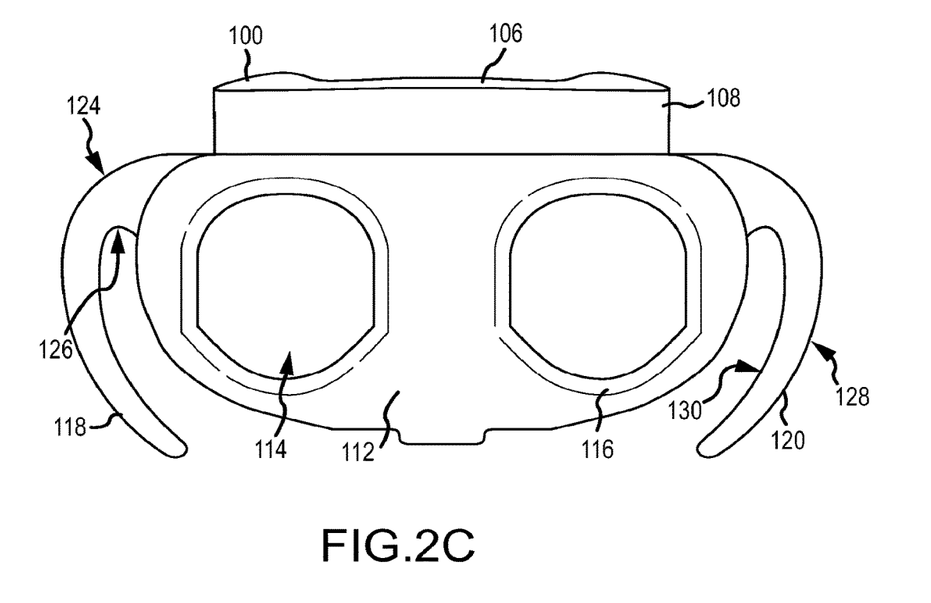
FIG. 2C is a front elevation view of the button latch of FIG. 2A with integrally molded cantilevered springs.

A female fluid connector may be used conjunction with male bayonet connectors to releasably connect sections of tubing. In one embodiment, for example as shown in FIGS. 1-2C, the female receiving connector 102 includes a button latch 100 that actuates an integral, guillotine-type latch plate 112. The latch plate 112 physically secures a male bayonet connector 104 within the female connector 102. When the male bayonet connector 104 is inserted distally into the female receiving connector 102, a distal end of the male bayonet connector 104 interfaces with a proximal edge of a receiving aperture 114 within the latch plate 112 to bias the latch plate 112 downward and lower the receiving aperture 114 through which the male bayonet connector 104 may pass. The downward travel of the latch plate 112 is countered by an arrangement of cantilevered springs 118, 120, 122 (see FIGS. 2A-2C) extending from the button actuator 106 and interfacing with surfaces on the interior walls of the housing of the female connector 102 in order to bias the latch plate 112 in an upward, locked position. The male bayonet connector 104 defines an annular channel 142 that is engaged by the edges of the aperture 114 in the guillotine latch plate 112 upon sufficient insertion of the male bayonet connector 104 into the female receiving connector 102.

The orientations "proximal" and "distal" as used herein have been arbitrarily chosen, and are not meant to limit the present disclosure, but will follow the convention just described with reference to the ends of the female receiving connector 102 and male bayonet connector 104.

In this embodiment, the female connector 102 is primarily designed for connection between the tubing from a blood pressure monitor and a male connector, which is attached to tubing from a blood pressure cuff. The blood pressure cuff is fastened about the patient's arm. When the female connector 102 is connected to the male connector 104, the flow of air can pass through. The term "dual lumen" indicates that there are two air pathways within the connector. Disconnect between the female connector 102 and the male connector 104 is achieved via pressing the actuation button latch 100, which disengages the male connector 104 from the latch plate 112 and then the two components can be pulled apart.

In the implementation depicted in FIGS. 1-5C, the button latch 100 has three cantilevered legs that function as springs, namely, a left spring 118, a right spring 120, and a rear spring 122. Each of the springs 118, 120, 122 is integrally formed with the actuator 106 and the latch plate 112. The latch plate 112 extends downwardly and generally perpendicularly from the proximal edge of the button actuator 106. The actuator 106 is a surface that resides within an aperture in the top of the housing of the female connector 102. The exposed surface of the actuator 106 may be ergonomically formed to support a thumb or finger of a user when depressing the actuator 106 to disengage the male connector 104. The actuator 106 may have a thickness defined by a sidewall 108 that interfaces with and travels along a corresponding sidewall of the aperture within the housing of the female connector 102. The actuator 106 may also define a retention flange 110 that extends outwardly at the base of the sidewall 108 underneath the top surface of the female connector housing to engage the housing and retain the button 100 within the apertures.

Each of the left spring 118 and the right spring 120 extend from a top lateral corner of the latch plate 112 and curve downwardly to a distance below the bottom of the latch plate 112. Each of the left and right springs 118, 120 may be understood as having an outer shoulder 124, an inner hollow 126, an outer radius 128, and an inner radius 130. There is thus a curved separation space between the inner radius 130 and the lateral sides of the latch plate 112. This separation space allows the left and right springs 118, 120 to flex when under pressure from the downward force of the button 100, either through depression of the actuator 106 by a user or due to the insertion of a male connector 104.

Figure 3A:
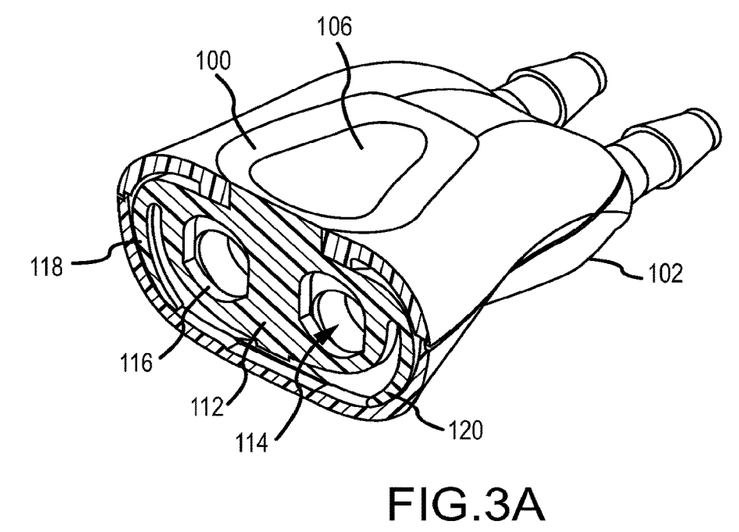
FIG. 3A is a top front isometric view in partial cross section of the button latch of FIG. 2 positioned in the female connector of FIG. 1.
Figure 3B:
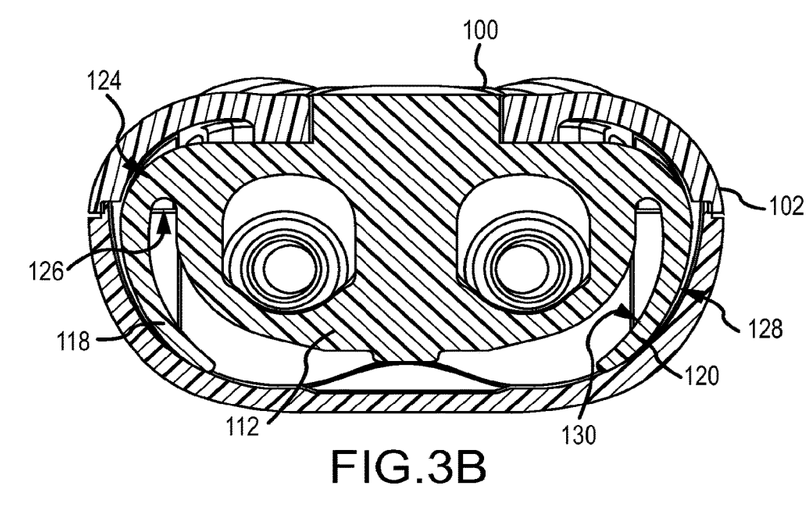
FIG. 3B is a front elevation view in cross section of the button latch of FIG. 2 positioned in the female connector of FIG. 1.

As shown in FIGS. 3A and 3B, the outer radius 128 of each toward the lower ends of the left and right springs 118, 120 interfaces with an inside surface of the housing of the female connector 102 as it transitions along a curve from side surfaces to the bottom surface of the housing. As the button is depressed, the left and right springs 118, 120 slide along the curved inner surface of the housing and deflect both laterally inward and upward.

Figure 3C:
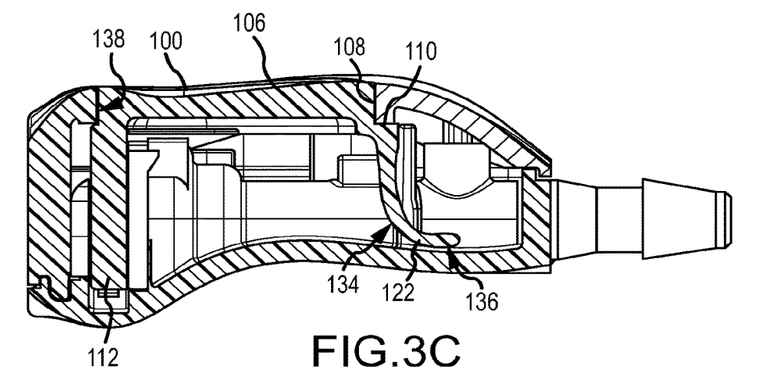
FIG. 3C is a side elevation view in cross section of the button latch of FIG. 2 positioned in the female connector of FIG. 1.

In addition to the left and right springs 118, 120, the rear of the button 100 is further supported by a rear spring 122 to provide a "tripod" support structure. The rear spring 122 curves distally outward from the button 100 rather than underneath it as the left and right springs 118, 120 do. The curve of the rear spring may be understood to define a rear spring outer radius 134. As shown in FIG. 3C, the outer radius 134 of the rear spring 122 interfaces with a curved inside surface of the housing of the female connector 102.

As the button is depressed, the rear spring 122 slides along the curved inner surface of the housing and deflects both distally and upward.

The button 100 is constantly biased upward due to the three springs 118, 120, 122. The springs 118, 120, 122 need to be "loaded" so that the button 100 remains in the upward or locked position until the user depresses the button 100 or until a male bayonet connector in inserted into the connector aperture 114, which will mechanically force the button 100 downward. The interface between the retention flange 110 and a guide wall 138 of the housing of the female connector 102 surrounding the button aperture therein ensures that the button 100 is retained within the female connector while under the bias of the springs 118, 120, 122. The thickness of the actuator 106 and therefore the height of the sidewalls 108 may be selected to be larger than the downward travel distance of the button 100 within the guide wall 138 when connecting and disconnecting with the male connector 104. In this way the sidewall 108 acts as a guide to align the button 100. The button 100 remains centered and level within the female connector 102 while it is depressed and further the actuator 106 does not slip under the housing of the female connector 102 to become stuck or misaligned.

Curved leading latch surfaces 116 located on the proximal side of the latch plate 112 on the bottom edge and lower sidewalls of the aperture 114 enable the button 112 to be actuated to its "down" position as the male bayonet connector 104 is inserted into the female connector 102. The distal end of the male connector 104 may be similarly curved or chamfered to aid in sliding past the latch surface 116.

Figure 4A:
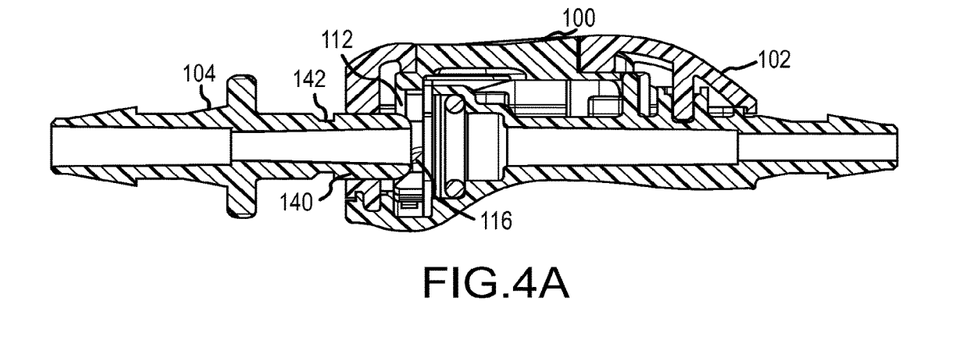
FIG. 4A is a side elevation view in cross section of the button latch of FIG. 2 positioned in the female connector of FIG. 1 initially receiving the male bayonet connector.

FIG. 4A illustrates a male bayonet connector 104 entering the aperture of the female connector housing 102. In some embodiments, the male bayonet connector 104 may include a proximal portion shaped as a barbed frustum for coupling with fluid tubing. The distal portion 140 of the male connector 104 may be generally cylindrical with a substantially smooth surface that may serve as a sealing surface when the male bayonet 104 is fully inserted into the female receiving connector 102. The male connector 104 may also have an annular channel 142 located proximal to and adjacent the distal portion 140. The annular channel 142 may be defined by sidewalls that are perpendicular or beveled with respect to the axis of the lumen of the male connector 104 that may be used to engage the latch plate 112.

Figure 4B:
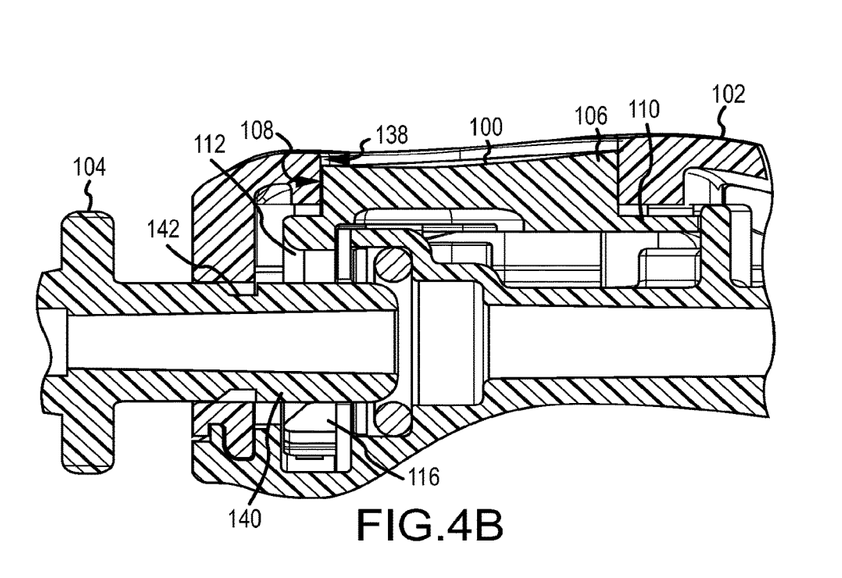
FIG. 4B is a side elevation view in cross section of the button latch of FIG. 2 positioned in the female connector of FIG. 1 with the male bayonet connector deflecting the button latch as it is inserted within the female connector.
Figure 4C:
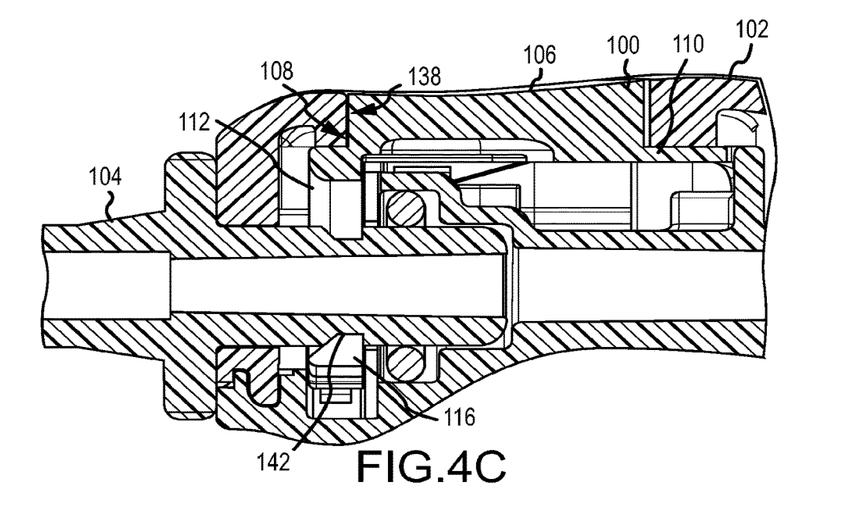
FIG. 4c is a side elevation view in cross section of the button latch of FIG. 2 positioned in the female connector of FIG. 1 with the male bayonet connector fully inserted within the female connector and the button latch engaging the male bayonet connector.

As the distal portion 140 of the male bayonet connector 104 enters into the female connector 102, it contacts the latch surface 116 of the connection aperture 114 as shown in FIG. 4B. As axial force is applied to insert the male bayonet connector 104 through the aperture 114, the latch plate 112 is forced downward against the opposing bias of the right, left, and rear springs 118, 120, 122 as the distal portion 140 slides against the ramped or curved latch surface 116. The latch plate 112 moves downward until the male bayonet connector 104 is able to pass through the larger area of the aperture 114. The male bayonet connector 104 extends through the aperture 114 until the annular channel 142 of the male bayonet connector 104 is aligned with the latch surface 116 of the latch plate 112 as shown in FIG. 4C. When the channel 142 is aligned with the latch plate 112, the latch plate 112 is forced upward by the springs 118, 120, 122 whereby the latch plate 112 engages the channel 142 to secure the male bayonet connector 104 within the female receiving connector 104.

The above descriptions demonstrate the need for the springs 118, 120., 122 to maintain their spring force and resiliency and resist creep, otherwise the female connector 102 will not securely engage and retain the male connecotr 102. Such female connectors 102 will typically see 20,000 male connects and 20,000 disconnects during a product life. The button 100 is mechanically depressed by the male bayonet 104 during insertion and the end user must manually depress the button to the "down" position to disconnect. Therefore, the product will typically see the button 100 depressed to its "down" position 40,000 times during its life.

A standard product specification is a tension pull load test. While the male connector 104 is locked into the female connector 104, the two are pulled apart. It is desirable that the connection withstand a 10 lb. tension axial pull load. Another typical product specification is the male insertion force. It is desirable that the force required to connect the male connector be lower than 4 lbs. A further typical product specification is the squeeze-to-disconnect force, i.e., button push-down force. It is desirable that the force not exceed 3.5 lbs.

There is a direct relationship between the spring force, the button push-down force, and the force required to connect the male. If the spring force increases, the push-down and insertion forces increase. If the spring force decreases, the push-down and insertion forces decrease. If the initial spring force is too low, there is a risk of the springs creeping or relaxing or deforming over time. The springs 118, 120, 122 need to maintain enough spring force to lift the button 100 to its "up" or "locked" position throughout the lifecycle of the female connector 102, i.e., for 40,000 depressions.

In one exemplary implementation, acetal plastic may be used for the molded button as well as the male connector 104 and/or the female connector housing 102. Acetal has very good shape memory and a high creep resistance. Acetal also has a low coefficient of friction which helps keep the insertion force low as the acetal male connector 104 makes contact with the latch surface 116 of the latch plate 112 and similarly as the springs 118, 120, 122 slide against the inner surface of housing of the female connector 102.

The springs 118, 120, 122 are designed so that the resultant stress is distributed over a large percentage of the spring's surface to minimize deformation of the springs 118, 120, 122 over extended use. See e.g., FIG. 5A for a finite element analysis of a desirable force distribution. The design of the three springs 118, 120, 122 is based upon a delicate balance between minimizing the spring force (to maintain the desirable push-down and male connection forces) and creating a geometry that will return to the original shape even after 40,000 actuations.

Figures 5A, 5B:
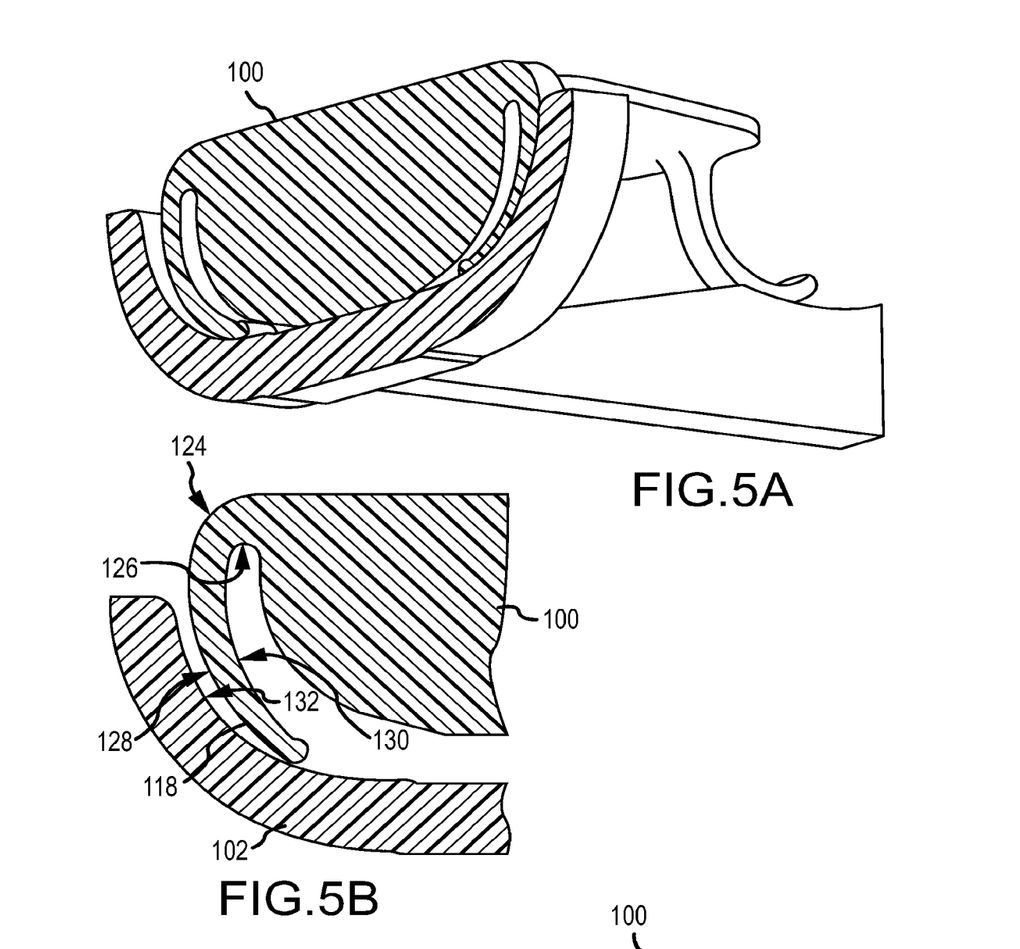
FIG. 5A is an illustration of finite element analysis results indicating areas of stress on the integrally molded springs on the button latch.
FIG. 5B is a schematic drawing of a spring arm of the button latch in a rest position.
Figure 5C:
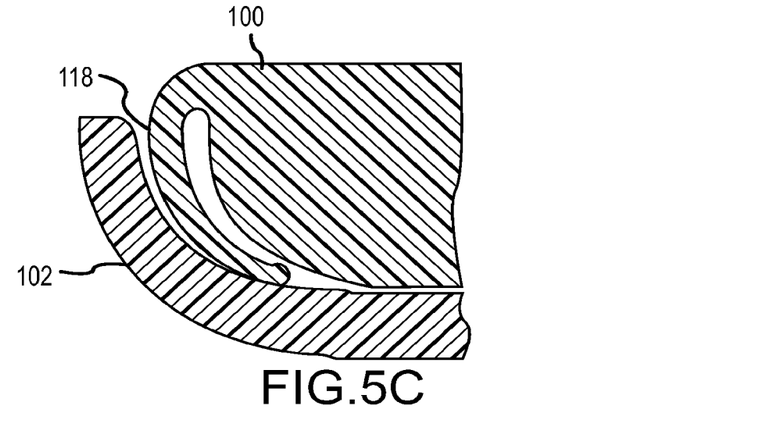
FIG. 5C is a schematic drawing of a spring arm of the button latch in a deformed position.

FIGS. 5B and 5C depict how the left and right springs 118, 120 of the present embodiment slide along the mating housing in both a vertical and horizontal direction as the button 100 is depressed downward. The mating geometry which enables the spring(s) to move in both a vertical and horizontal is significant to achieve the low push-down and insertion forces, as well as distributing forces through the springs in such a way that it minimizes flexural creep and deformation of the spring(s) over repeated use.

Through finite element analysis and actual testing, a desirable relationship between the radius of curvature of the outer shoulder 124 to the radius of curvature of the inner hollow 126 at the base of the left and right springs 118, 120 has been determined as a ratio in a range between 5.40 and 9.67 for the springs 118, 120 of this implementation to adequately perform.

Similarly, through finite element analysis and actual testing, a desirable relationship between the outer radius of curvature 128 to the inner radius of curvature 130 of the left and right springs 118, 120 has been determined as a ratio in a range between 1.06 and 1.22 for the left and right springs 118, 120 of this implementation to adequately perform.

Further, through finite element analysis and actual testing, a desirable relationship between the outer radius of curvature 128 of the left and right springs 118, 120 to the radius of curvature 132 of the mating surface on the connector housing has been determined as a ratio in a range between 1.06 and 1.22 for the left and right springs 118, 120 of this implementation to adequately perform.

Additionally, through finite element analysis and actual testing, a desirable relationship between the radius of curvature 132 of the mating surface on the connector housing to the outer radius of curvature 128 of the rear spring 122 has been determined as a ratio in a range between 6.44 and 8.30 for the rear spring 122 of this implementation to adequately perform.

Additional implementations of button latches with integrally molded cantilevered springs are possible. Several additional examples of such implementations are presented in FIGS. 6A-8B. As before, the molded in cantilever springs are designed to simplify a button latch where helical or other coil springs would normally be used to force the button to return to its resting position after being pushed down in some fashion. Each of the following examples is a button with molded springs that provide specific return forces and/or resistances to push-down and may be designed to meet particular specifications.

Figure 6A:
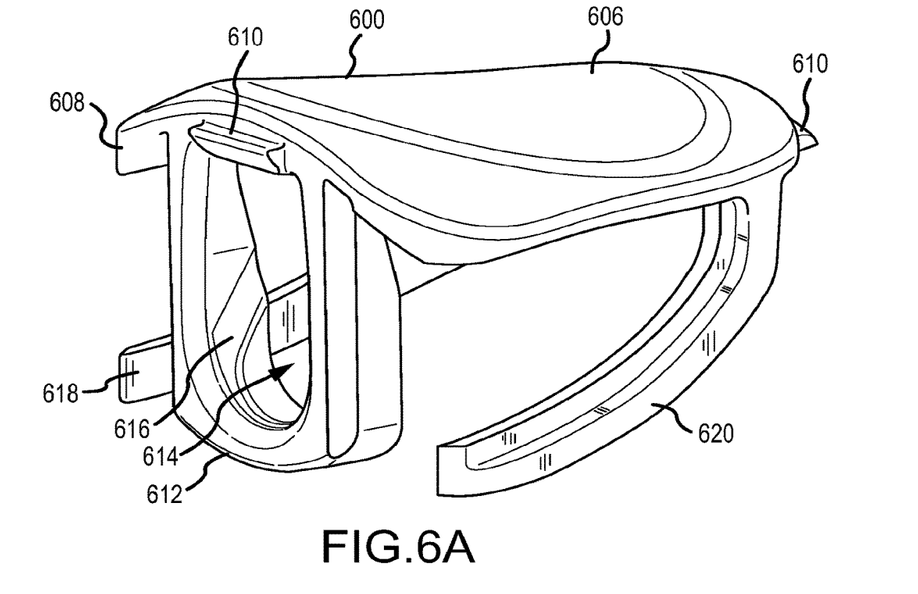
FIG. 6A is an isometric view of a second embodiment of a button latch with integrally molded cantilevered springs.

FIGS. 6A depicts an exemplary implementation of a button 600 that pivots or is hinged in the rear and allows for the front portion of the button 600 to move. The button 600 is composed of an actuator 606 with short sidewalls 608, a retention tab 610 on the proximal end, and a hinge tab 622 on the distal end to retain the button 600 within the housing of the connector.

The left and right cantilever leg springs 618, 620 have a form similar to sleigh runners. In this embodiment, the springs 618, 620 have a right angle channel cross section for structural reinforcement. The left and right springs 618, 620 may be formed with various cross sections to achieve desired levels of spring force, structural rigidity, and creep resistance. The left and right springs 618, 620 attach to the button actuator 606 at the distal end and sweep downward and proximally underneath the actuator 606. As in the prior embodiment, the button 600 has a latch plate 612 with a sloping latch surface 616 that defines an aperture 614 for receipt of and connection with a male connector.

FIGS. 6B-6H depict the button 600 disposed within a female connector housing composed of an upper housing 602 and a lower housing 604 that are connected together, e.g., by ultrasonic welding, adhesive, detent tabs, or otherwise. The upper housing 602 defines a connector aperture 638 at the proximal end that provides access for a male connector. The lower housing defines a connector lumen 640 that is in fluid communication with the connector aperture 638 on the proximal end and with a barb lumen 644 defined within a barb fitting section 644 on the distal end. In this embodiment, the barb fitting section 642 is integrally formed as a part of the lower housing 604 and is configured for retaining a flexible fluid tube thereon. The retention tab 610 halts the upward travel of the button 600 under bias of the springs 618, 620 upon interfacing with a retention surface 628 in the upper housing 602. The hinge tab 622 is retained under and pivots against a bearing surface 624 of the upper housing 602 as the button 600 is pushed downward by a user.

Figure 6B:
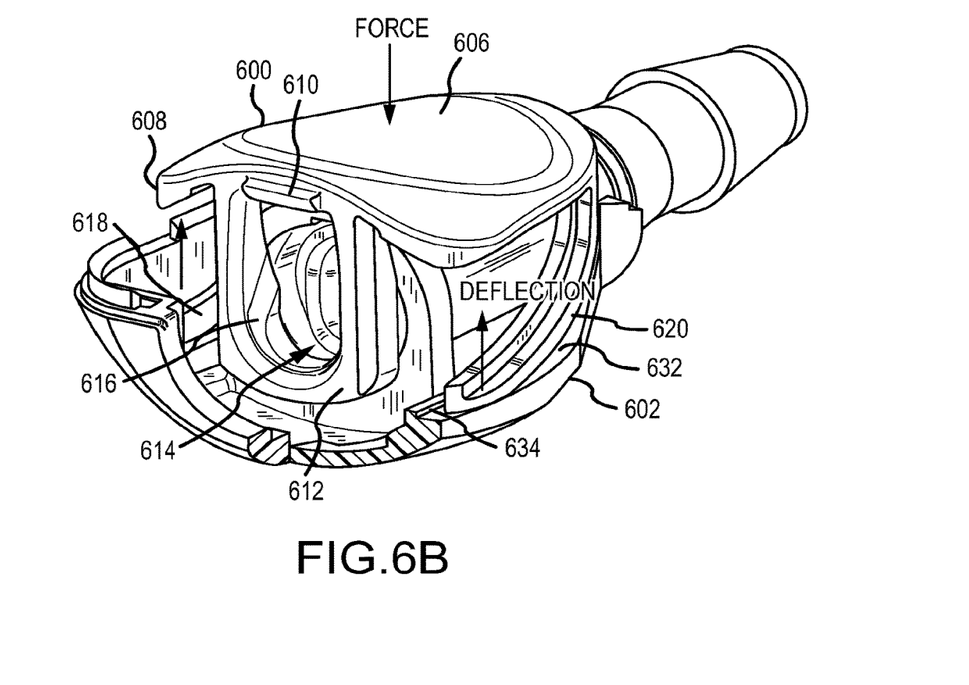
FIG. 6B is an isometric view of the second embodiment of the button latch positioned within a female connector housing shown in partial cross section.
Figures 6C, 6D:
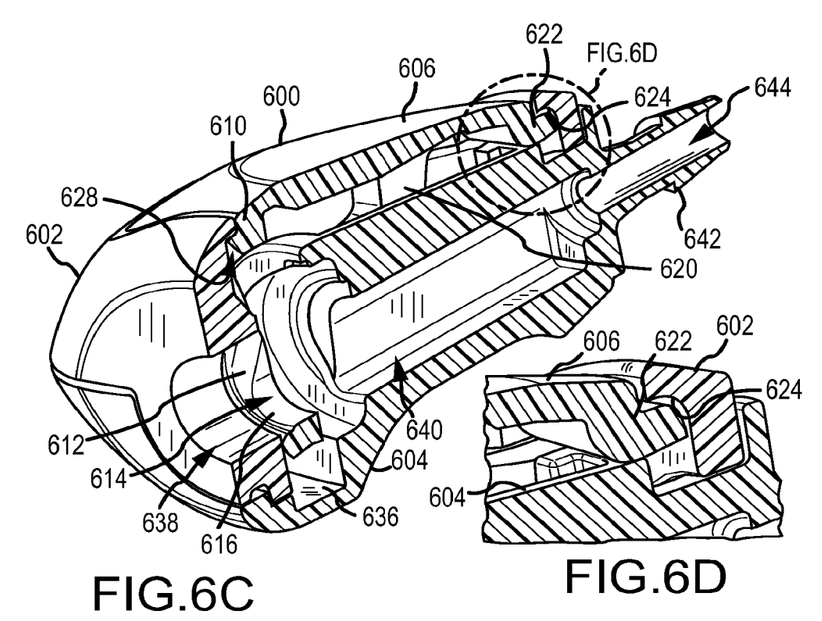
FIG. 6C is an isometric view of the second embodiment of the button latch positioned within a female connector housing shown in partial cross section.
FIG. 6D is an enlarged view of a portion of the second embodiment of the button latch as indicated in FIG. 6C.
Figures 6E, 6F:
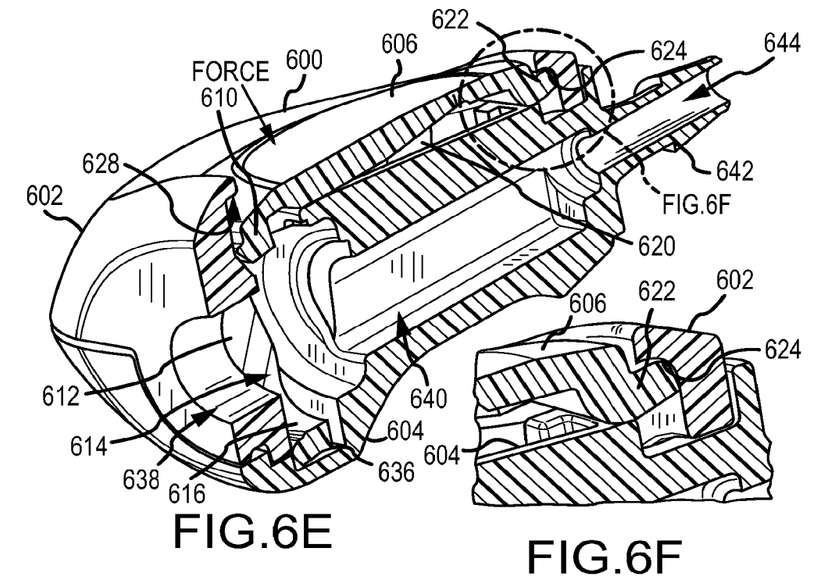
FIG. 6E is an isometric view of the second embodiment of the button latch positioned within a female connector housing shown in partial cross section with the button in a depressed position.
FIG. 6F is an enlarged view of a portion of the second embodiment of the button latch as indicated in FIG. 6E.
Figure 6G:
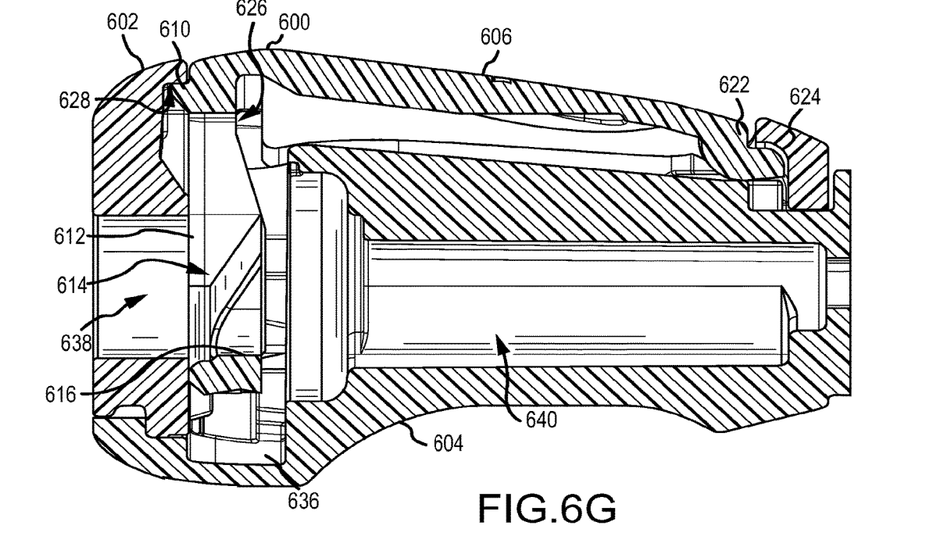
FIG. 6G is a side elevation view in cross section of the second embodiment of the button latch positioned within a female connector housing.
Figure 6H:
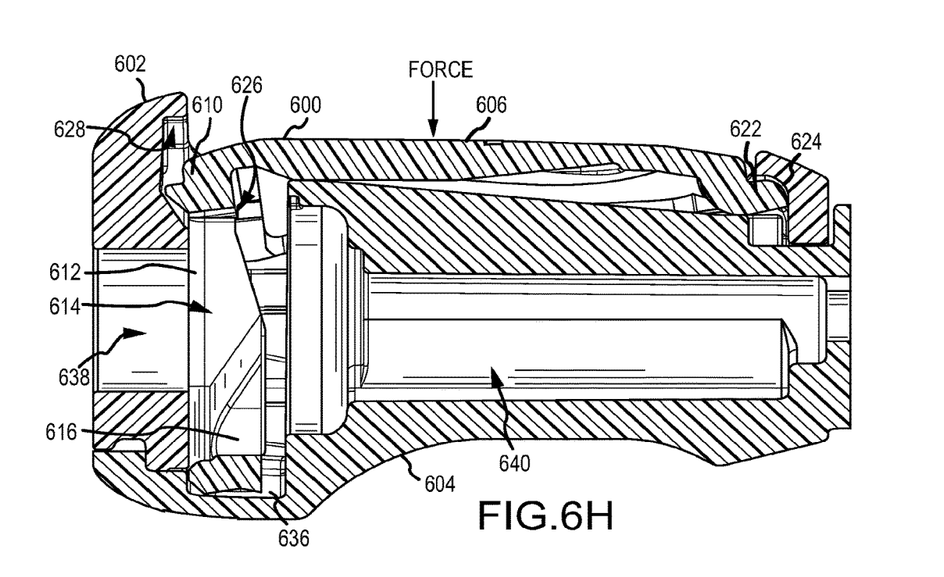
FIG. 6H is a side elevation view in cross section of the second embodiment of the button latch positioned within a female connector housing with the button in a depressed position.

The left and right leg springs 618, 620, as shown in FIG. 6B, extend to a point below the proximal end of the button 600 on either side of the latch plate 612. This position provides the largest vertical travel distance for the button 600, minimizes the forward rocking motion of the button 600, and provides a good, stable feel to the push-down motion. The springs 618, 620 deflect upwards as indicated by the arrows in FIG. 6B under a downward force on the actuator 606. The leg springs 618, 620 also slide proximally within a guide track 632 formed in the bottom wall of the female connector housing 602. A shallow guide wall 634 may also be formed in the housing 602 to prevent the leg springs 618, 620 from angling inward. Such restraint may be desirable to limit the vertical travel of the button 606 or as another method for resisting creep by limiting lateral movement of the leg springs 618, 620. The bias in the left and right leg springs 618, 620 will force the button to return up to its resting position when the user force is removed from the button 600.

As noted, the button 600 pivots at the interface of the hinge tab 622 and the bearing surface 624 under the downward force on the actuation surface 606. As the latch plate 612 travels downward within a latch channel 636 formed within the upper housing 602 and lower housing 604, the latch plate 612 flexes along a flexion area 626 at the interface between the latch plate 612 and retention tab 610 on the button 600. The flexion area 626 is formed as a thinner section of the latch plate 612 and allows the latch plate 612 to flex and maintain a constantly vertical orientation in view of the constraints of the latch channel 636 even though the movement of the proximal end of the button 600 is angular downward and distally due to the hinge structure of the hinge tab 622 at the distal end of the button 600. By maintaining a vertical orientation of the latch plate 612 within the latch channel 636, a better locking interface between the latch surface 616 and the inserted male connector is achieved.

Figure 7A:
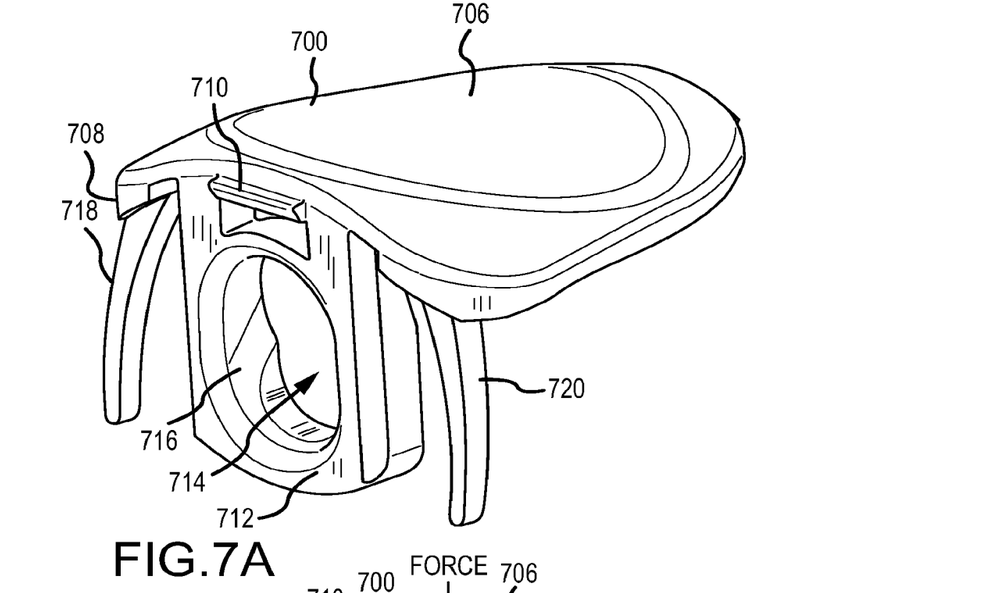
FIG. 7A is an isometric view of a third embodiment of a button latch with integrally molded cantilevered springs.

FIG. 7A is another exemplary implementation of a button 700 that slides vertically along cantilevered leg springs 718, 720 extending from the lateral proximal edges of the button 700. The button 700 is composed of an actuator 706 with short sidewalls 708 and retention tabs 710 on the proximal and distal ends to retain the button 700 within the housing of the connector. The left and right cantilever leg springs 718, 720 are curved slightly laterally outwardly, but primarily extend downwardly substantially normal to the actuator 706. As in the prior embodiment, the button 700 has a latch plate 712 with a sloping latch surface 716 that defines an aperture 714 for receipt of and connection with a male connector.

Figure 7B:
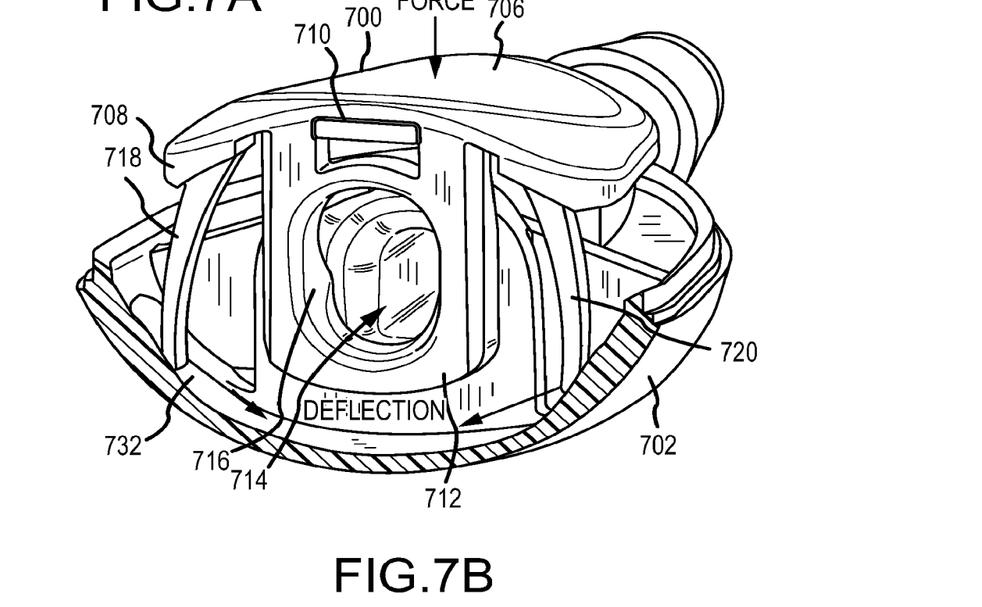
FIG. 7B is an isometric view of the third embodiment of the button latch positioned within a female connector housing shown in partial cross section.

FIG. 7B depicts the button 700 disposed within a female connector housing 702. The left and right leg springs 718, 720, as shown in FIG. 7B, extend to a point below the proximal end of the button 700 on either side of the latch plate 712. The springs 718, 720 deflect laterally inwards and move symmetrically toward each other as indicated by the arrows in FIG. 7B under a downward force on the actuator 706. The leg springs 718, 720 also slide laterally along a guide surface 732 formed in the bottom wall of the female connector housing 702. The guide surface 732 may be formed in a similar manner to a cam surface in that the guide surface 732 can be designed to push the springs closer together or release tension based upon the thickness of the wall at various points along the guide surface 732. Such variations in the guide surface 732 may be desirable to change (e.g., increase) the force on the button 706 as the springs travel 718, 720 or as another method for resisting creep by limiting lateral movement of the leg springs 718, 720. The bias in the left and right leg springs 718, 720 will force the button to return up to its resting position when the user force is removed from the button 700.

Figure 8A:
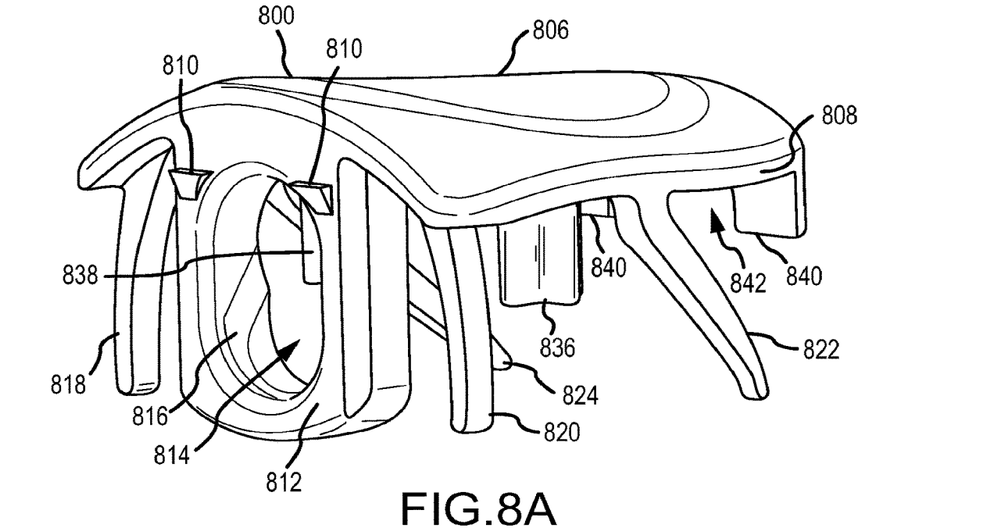
FIG. 8A is an isometric view of a fourth embodiment of a button latch with integrally molded cantilevered springs.

FIG. 8A is another exemplary implementation of a button 800 that slides vertically along cantilevered leg springs 818, 820 extending from the lateral proximal edges of the button 800. This embodiment of a button 800 is very similar to the prior embodiment of the button 700 with the addition of two rear springs 822, 824 and several additional alignment features. The button 800 is composed of an actuator 806 with short sidewalls 808 and retention tabs 810 on the proximal end to retain the button 800 within the housing of the connector. Additionally, a pair of rear alignment walls 840 extends downwardly from the distal end of the actuator 806 defining a curved saddle therebetween. Retention tabs (not shown) are also on the distal faces of the rear alignment walls 840. A pair of guideposts 836, 838 also extends downward, normal to the bottom surface of the actuator 806. The left and right cantilever leg springs 818, 820 are curved slightly laterally outwardly, but primarily extend downwardly substantially normal to the actuator 806. As in the prior embodiment, the button 800 has a latch plate 812 with a sloping latch surface 816 that defines an aperture 814 for receipt of and connection with a male connector. In this embodiment, two additional cantilevered rear springs 822, 824 extend slightly downward from the center of the sidewalls of the actuator and then form shoulders from which they extend downward at a distal angle.

Figure 8B:
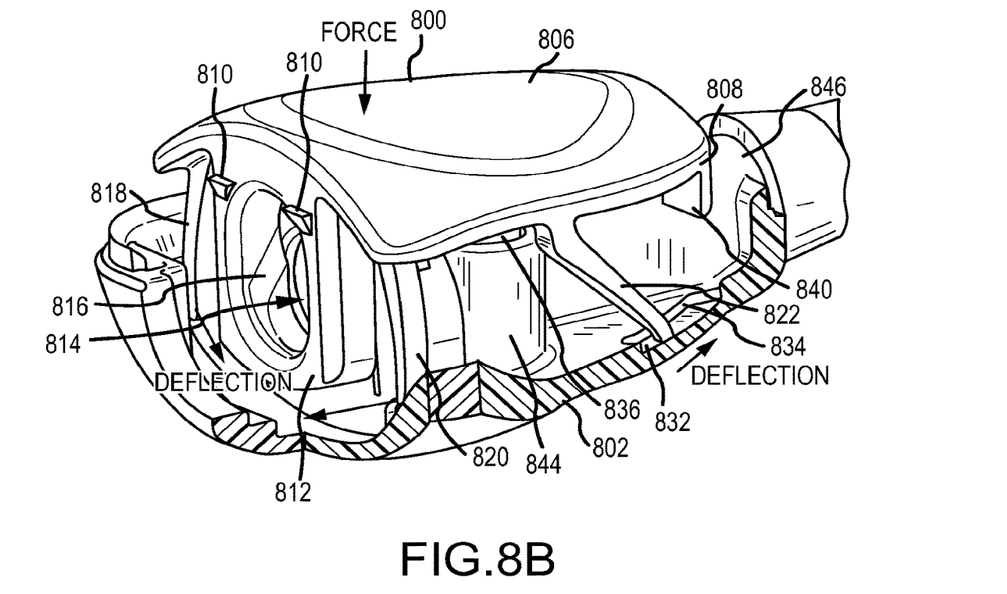
FIG. 8B is an isometric view of the fourth embodiment of the button latch positioned within a female connector housing shown in partial cross section.

FIG. 8B depicts the button 800 disposed within a female connector housing 802. The left and right leg front springs 818, 820, as shown in FIG. 8B, extend to a point below the proximal end of the button 800 on either side of the latch plate 812. The springs 818, 820 deflect laterally inwards and move symmetrically toward each other as indicated by the arrows in FIG. 8B under a downward force on the actuator 806. The left and right leg springs 818, 820 also slide laterally along a surface in the bottom wall of the female connector housing 802. The bias in the left and right leg springs 818, 820 will force the button 800 to return up to its resting position when the user force is removed from the button 800. The rear leg springs 822, 824 also slide distally within a guide track 832 formed in the bottom wall of the female connector housing 802 while resisting the downward force on the button 800. A shallow guide wall 834 may also be formed in the housing 802 to prevent the rear leg springs 818, 820 from angling inward. Such restraint may be desirable to limit the vertical travel of the button 806 or as another method for resisting creep by limiting lateral movement of the leg springs 818, 820. The bias in the rear leg springs 822, 824 will force the button 800 to return up to its resting position when the downward user force is removed from the button 800.

In addition, the guideposts 836, 838 may be aligned with and fit within cylindrical guide tubes 844 extending upward from the bottom of the housing 802. The interface between the guideposts 836, 838 and the guide tubes 844 helps maintain the vertical alignment of the button 800 within the female connector housing 802 and may further be used to limit the vertical travel distance of the button. Further, the saddle 842 formed between the rear alignment walls 840 may be used to align the button 800 with a wall of a lumen 846 formed within the female connector 802.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A button latch for use in a fluid connector, the button latch comprising:
   a button actuator portion for engagement by a user;
   a latch plate integrally formed with and extending downwardly and perpendicularly from a proximal edge of the button actuator portion and configured to physically secure a male connector within the button latch; and
   a plurality of cantilevered leg springs, each leg spring integrally formed with the button actuator portion and the latch plate and cantilevered from either a bottom surface of the button actuator portion or both an upper portion of the latch plate and the bottom surface of the button actuator portion,
   wherein the plurality of cantilevered leg springs comprise two leg springs extending symmetrically downward and inward from laterally opposite corners of the button actuator portion to bias the latch plate in a locked position and resist depression forces applied to each of the button actuator portion and the latch plate,
   wherein the plurality of leg springs further comprise two leg springs extending downward and angled rearward from laterally opposite sides of the button actuator portion.

2. The button latch of claim 1, wherein the two leg springs curve symmetrically downward and inward to extend under the latch plate.

3. The button latch of claim 2, wherein the two leg springs each have an outer shoulder and an inner hollow and a ratio of a radius of curvature of the outer shoulder to a radius of curvature of the inner hollow is between 5.40 and 9.67.

4. The button latch of claim 2, wherein a ratio of an outer radius of curvature of one of the leg springs to an inner radius of curvature of the one of the leg springs is between 1.06 and 1.22.

5. The button latch of claim 2, wherein the plurality of leg springs further comprise a rear leg spring extending downward from a bottom of the button actuator portion and curving distally.

6. The button latch of claim 1, wherein the two leg springs extend downward in substantially a same plane as the latch plate.

7. The button latch of claim 1 further comprising a hinge tab extending from a rear edge of the button actuator portion configured for engagement with a bearing surface on a housing of the fluid connector.

8. The button latch of claim 1 further comprising an alignment post extending downward from a bottom surface of the button actuator portion configured to engage with a post receiver in the fluid connector.

9. The button latch of claim 8, wherein the alignment post is positioned along a rear edge of the button actuator portion.

10. The button latch of claim 1 further comprising a retention tab positioned along a front edge of the button actuator portion and configured to retain the front edge of the button actuator portion within a housing of the fluid connector.

11. A button latch for use in a fluid connector, the button latch comprising:
- a button actuator portion for engagement by a user;
- a latch plate integrally formed with and extending downwardly and perpendicularly from a proximal edge of the button actuator portion and configured to physically secure a male connector within the button latch; and
- a plurality of cantilevered leg springs, each leg spring integrally formed with the button actuator portion and the latch plate and cantilevered from either a bottom surface of the button actuator portion or both an upper portion of the latch plate and the bottom surface of the button actuator portion,
- wherein the plurality of cantilevered leg springs comprise two leg springs extending symmetrically downward and inward from laterally opposite corners of the button actuator portion to bias the latch plate in a locked position and resist depression forces applied to each of the button actuator portion and the latch plate,
- wherein the plurality of leg springs further comprise two leg springs extending downward from laterally opposite sides of the button actuator portion and further curving forward to extend along a length of the button actuator portion toward the latch plate.

12. A fluid tubing connector, comprising:
a housing defining an aperture in a top surface thereof;
a tube connection portion;
an opening configured to receive a male connector;
a button latch configured to engage and disengage with the male connector, the button latch further comprising:
- a button actuator portion with a top surface exposed within the aperture in the top surface of the housing for engagement by a user;
- a latch plate integrally formed with and extending downwardly and perpendicularly from a proximal edge of the button actuator portion and defining a latch aperture substantially aligned with the opening, wherein the latch plate is configured to engage a male connector to secure the fluid tubing connector in a locked position;
- a plurality of cantilevered leg springs, each leg spring integrally formed with the button actuator portion and the latch plate, extending from either a bottom surface of the button actuator portion or both an upper portion of the latch plate and the bottom surface of the button actuator portion, and contacting an inner wall surface of the housing; and
- a hinge tab extending from a rear edge of the button actuator portion configured for engagement with a bearing surface on an edge of the housing defining the aperture in the top surface,
- wherein the plurality of cantilevered leg springs comprise two leg springs extending symmetrically downward and inward from laterally opposite corners of the button actuator portion to bias the latch plate within the housing in the locked position and resist depression forces applied to each of the button actuator portion and the latch plate.

13. The fluid tubing connector of claim 12, wherein the plurality of leg springs comprise two leg springs extending laterally from opposing top corners of the latch plate and curving symmetrically downward and inward to extend under the latch plate and to slidingly engage the inner wall surface of the housing.

14. The fluid tubing connector of claim 13, wherein the plurality of leg springs further comprise a rear leg spring extending downward from a bottom of the button actuator portion and curving distally to slidingly engage the inner wall surface of the housing.

15. The fluid tubing connector of claim 14, wherein a ratio of an outer radius of curvature of the rear leg spring to a radius of curvature of the inner wall surface of the housing is between 6.44 and 8.30.

16. The fluid tubing connector of claim 12, wherein the plurality of leg springs further comprise two leg springs extending downward and angled rearward from laterally opposite sides of the button actuator portion to slidingly engage the inner wall surface of the housing.

17. The fluid tubing connector of claim 12, wherein the two leg springs extend downward in substantially a same plane as the latch plate.

18. The fluid tubing connector of claim 12, wherein the plurality of leg springs further comprise two leg springs extending downward from laterally opposite sides of the button actuator portion and further curving forward to extend along a length of the button actuator portion toward the latch plate.

19. The fluid tubing connector of claim 12, wherein
the housing further defines a channel within which the latch plate translates upward and downward; and
an interface between the button actuator portion and the latch plate is pliable to allow the button actuator portion to bend with respect to the latch plate as the button actuator portion pivots on the hinge tab at the bearing surface when depressed.

20. The fluid tubing connector of claim 12 further comprising an alignment post extending downward from the bottom surface of the button actuator portion configured to engage with a post receiver formed on the inner wall surface of the housing.

21. The fluid tubing connector of claim 20, wherein the alignment post is positioned along a rear edge of the button actuator portion.

22. The fluid tubing connector of claim 12 further comprising a retention tab positioned along a front edge of the button actuator portion and configured to engage an edge of the housing defining the aperture in the top surface to retain the front edge of the button actuator portion within the housing.

23. The fluid tubing connector of claim 12 further comprising one or more channels formed in the inner wall surface of the housing configured to interface with and guide movement of one or more respective ones of the plurality of cantilevered leg springs when the button actuator portion is depressed.

24. The fluid tubing connector of claim 12, wherein the two leg springs each have an outer shoulder and an inner hollow and a ratio of a radius of curvature of the outer shoulder to a radius of curvature of the inner hollow is between 5.40 and 9.67.

25. The fluid tubing connector of claim 12, wherein a ratio of an outer radius of curvature of one of the leg springs to an inner radius of curvature of the one of the leg springs is between 1.06 and 1.22.

26. The fluid tubing connector of claim 12, wherein a ratio of an outer radius of curvature of one of the leg springs to a radius of curvature of a corresponding mating surface on the inner wall surface of the housing of the fluid tubing connector is between 1.06 and 1.22.

* * * * *